United States Patent [19]

Zagnoli

[11] Patent Number: 4,755,533

[45] Date of Patent: Jul. 5, 1988

[54] TOPICAL VAGINAL USE OF LYSINE P-ISOBUTYLPHENYLPROPIONATE IN ANTI-INFLAMMATORY TREATMENT

[75] Inventor: Giorgio Zagnoli, Como, Italy

[73] Assignee: Laboratorio Italiano Biochimico Farmaceutico LISAPHARMA SpA, Erba, Italy

[21] Appl. No.: 44,282

[22] Filed: Apr. 30, 1987

[30] Foreign Application Priority Data

Jun. 16, 1986 [IT] Italy ............................... 20797 A/86

[51] Int. Cl.$^4$ .......................................... A61K 31/195
[52] U.S. Cl. ..................................................... 514/561
[58] Field of Search ........................................ 514/561

[56] References Cited

PUBLICATIONS

Chem. Abst. 84 (1976)–22096x and 85–68288k (1976).

*Primary Examiner*—Stanley J. Friedman
*Attorney, Agent, or Firm*—Parkhurst & Oliff

[57] ABSTRACT

This invention relates to the vaginal topical use of lysine p-isobutylphenylpropionate in local and targeted anti-inflammatory treatment of pathologies of obstetric and gynelogical type.

Said use is effective in the treatment of patients with inflammatory forms having either aspecific or specific etiology, and also in the treatment both of patients of medical pertinence and of patients of surgical pertinence. The lysine p-isobutylphenylpropionate is used in the form of an aqueous solution for vaginal washes or in other pharmaceutical forms for vaginal use such as globules, suppositories etc.

2 Claims, No Drawings

TOPICAL VAGINAL USE OF LYSINE P-ISOBUTYLPHENYLPROPIONATE IN ANTI-INFLAMMATORY TREATMENT

This invention relates to a new therapeutic use for lysine p-isobutylphenylpropionate.

More particularly, the invention relates to the anti-inflammatory use of lysine p-isobutylphenylpropionate in topical gynecological therapy.

Lysine p-isobutylphenylpropionate, also called hereinafter by its commercial name ARFEN (a registered name of the firm LISAPHARMA of Erba, Como, Italy) is a known medicament widely used in arthrorheumatic and traumatologic illnesses and in painful manifestations of any origin, it being used for example in renewed acuteness of arthrosic and rheumatic pain, in post-traumatic pain resulting from contusions, distortions and muscular sprains, in toothache, in dysmenorrhea and in cephalea.

The effectiveness of ARFEN in the treatment of these pathological forms is widely illustrated in a large number of published works.

Up to the present time, it has been applied orally, parenterally and ionophoretically, in this latter case particularly in traumatic pathologies of sportsmen with a strong pain component.

We have now surprisingly discovered that ARFEN is unexpectedly effective in local and targeted anti-inflammatory treatment of various obstetric and gynecological pathological situations. It is well known that specific and aspecific gynecological phlogoses represent an important part of gynecological pathology.

Alteration of the vaginal environment nearly always results in the onset of colonisation of the vaginal lumen by bacterial species, by yeasts and by pathogenic protozoa. This alteration can depend on many factors:
reduction in the body defences (hemoblastosis, neoplasia, tuberculosis, Cushings syndrome etc.);
diabetic illness (by an increase in the glucose content of the epithelium and the vaginal secretion);
use of antibiotics with direct mycete stimulation or with destruction of the vaginal physiological flora;
poor local hygiene;
systemic and local contraceptive means.

Gynecological phlogoses are under continuous increase both for the aforesaid reasons and because of the considerable increase in the average life of women, and cannot always be viewed as a pathological phenomenon of irrelevant clinical importance. In this respect, the tendency for these symptoms to become chronic must result in a certain preoccupation, at least until the connection between recurrent phlogoses and the incidence of neoplasia has been completely clarified.

It is well known that gynecological phlogoses are often associated with infective pathology, deriving from mycetic, protozoan and/or bacterial etiology, these being absolutely indistinguishable from the symptomatologic aspect, they all being in any event under increase and no longer controllable because of the indiscriminate use of antibiotics and of the increasing distribution of estroprogestins.

In this context, if to this increased incidence is added the tendency of patients not to undergo specialist medical examination, and thus having no means of obtaining a reliable microscopic diagnosis which represents the only means for differentiating between aspecific and infective phlogistic forms, it is apparent that an anti-inflammatory preparation for topical use which is absolutely safe in terms of tolerance would occupy first place in the choice of the medical practitioner. In this respect, in the absence of a specific diagnosis it is preferable to initially use a product of antiphlogistic activity, even if this may be later replaced by more targeted products such as imidazoles, polyenics or antibiotics.

We have now found that these objectives are attained by using as specific medicament for gynecological inflammatory pathology ARFEN formulated as a vaginal wash or in other pharmaceutical forms for vaginal use such as globules, suppositories etc.

This type of treatment is also considered with favour for the following two reasons. The first reason refers to the aforegoing, ie possibility of therapeutically confronting a pathology before knowing its etiology and thus whether it derives from functional organic causes or from an infective factor. The second reason relates to the extreme ease of application of the product which, when formulated as a wash, or in other pharmaceutical forms, enables the appropriate therapeutic schemes to be conducted daily without any inconvenience. These results are obtained by the topical use in gynecological therapy of lysine p-isobutylphenylpropionate in the form of an aqueous solution for vaginal washes or in any other pharmaceutical form for vaginal application, for use in the local and targeted anti-inflammatory treatment of various obstetric and gynecological pathological situations. The characteristics of the solution, its methods of application and the results obtained are illustrated in the following applicative description, which is given by way of non-limiting illustration. This applicative description relates to research conducted in order to investigate whether ARFEN possesses the power to resolve gynecological phlogoses. In addition to its efficiency, its systemic and local tolerance level was also evaluated. ARFEN was formulated as a vaginal wash, with an accompanying endovaginal applicator, corresponding to the following quantitative composition:
lysine p-isobutylphenylpropionate: 1.4 g
trimethylcetylammonium p-toluenesulphonate: 0.014 g
red rose perfume: 0.14 ml
distilled water: to make up to 140 ml This composition can be varied according to requirements, both from the qualitative and quantitative aspect. For example, the composition can be varied within the following range:
lysine p-isobutylphenylpropionate: 0.5–2 g
trimethylcetylammonium p-toluenesulphonate: 0.005–0.02 g
red rose perfume: 0.05–0.2 ml
distilled water: to make up to 100 ml For comparison purposes a placebo of the following formulation was used:
trimethylcetylammonium p-toluenesulphonate: 0.014 g
red rose perfume: 0.14 ml
distilled water: to make up to 140 ml The patients were assigned to ARFEN or placebo treatment after randomisation in order to ensure perfect group homogeneity.

A total of 30 patients were involved in the research, their average age being 31.87±8.15 years (min 19, max 58).

In addition to a group of patients of medical pertinence, a group of patients of surgical pertinence was also involved in order to investigate whether pre-post operative prophylaxis in the gynecological field was desirable.

The patients were divided into 4 groups as follows:
(a) surgical group treated with placebo
(b) surgical group treated with ARFEN
(c) medical group treated with placebo
(d) medical group treated with ARFEN The patients of medical pertinence were treated once a day for 10 days, effecting the vaginal wash in the evening just before going to bed, in order to ensure protracted contact between the ARFEN and the vaginal mucosa for the entire night. The applications were continued for an average of 9.53±1.94 days (min 6, max 10).

For the patients of surgical pertinence, the prophylaxis scheme was as follows: 1 globule of terramycin the evening before the operation followed by the ARFEN wash in the morning one hour before the operation. These patients were in all cases treated antibiotically with curoxim at a dose of 1 g one hour before the operation, 1 g eight hours after the operation and 1 g twelve hours after the operation.

During the days following the operation, the antibiotic was administered to the extent of 1 g/day and the ARFEN wash was effected once a day.

The wash and antibiotic administration lasted an average of 9.53±1.94 days (min 6, max 10).

The following parameters were checked in the patients pertaining to the two "medical" groups, ie those not undergoing operation:
irritation
smarting
pain
leukorrhea
these being quantified by an arbitrary points system of between 0 and 3, on the following basis:
0=absence of symptom
1=symptom slight
2=symptom moderate
3=symptom intense The four symptomatologic tests were conducted at the following times: 0 (basal), 3, 5, 7 and 10 days from the commencement of the therapy.

The systemic tolerance study was conducted by periodically checking the following laboratory parameters before and after treatment:
leukocytes
erythrocytes
hemoglobin
hematocrit
platelets
glycemia
azotemia
transaminase (SGOT-SGPT)
alkaline phosphatase
uricemia In contrast, local tolerance was evaluated by measuring certain parameters related to intolerance of the preparation, such as pain or smarting at the moment of application, this evaluation therefore being entirely different from that more typically connected with the pathology.

On termination, an overall clinical judgement of the therapy was expressed, which also took account of the subjective judgement given by each patient.

For the patients pertaining to the two "surgical" groups, the evolution of the clinical symptomatology was investigated using the aforesaid parameters, evaluated by the same numerical code (0-1-2-3) and the same time intervals.

In addition, particular attention was given to cicatrization phenomena, including regression of the mucosa edema, which frequently accompanies gynecological surgery.

Systemic tolerance was investigated by laboratory tests as in the case of the preceding group, but at least for the first two days after the operation it was not considered valid for the local tolerance study to analyse any "pain" or "smartness" expressed by the patients because of the obvious connection with the surgical operation itself. The overall judgement expressed on termination of the experiment does not take account of any subjective aspects in the case of the "surgical" groups, but only of those aspects more typically connected with the cicatrization evolution of the tissues and of the mucosa concerned in the operation.

The investigation was therefore aimed at determining whether it was possible to act with preventive means in the resolution of phlogoses, which in the particular case of mucosa structures can easily become chronic, to result in symptoms which are sometimes severe and not easy to resolve.

All the individual data after suitable tabulation were analysed statistically by the Student "t" test, which was able to be applied correctly because the various symptomatologic parameters had been semi-quantitatively expressed by means of an arbitrary points system.

Tables 1, 2, 3 and 4 show the characteristics of the treated cases with details of the individual group data concerning diagnoses and type of operation (for surgical groups), treatment duration and final clinical judgement.

TABLE 1

Case characteristics: Group a (surgical group treated with placebo)

| Case No. | Age (years) | Therapy duration | Type of operation | Associated therapy | Clinical judgement |
|---|---|---|---|---|---|
| 1 | 34 | 10 days | myomectomy | * | mediocre |
| 2 | 33 | 10 days | adnexectomy sx salpingectomy dx | * | good |
| 3 | 34 | 10 days | salpingoplasty myomectomy | * | good |
| 4 | 29 | 6 days | ovarian cyst removal | * | mediocre |
| 5 | 31 | 10 days | marsupialisation dx external | * | unsatisfact. |
| 6 | 31 | 10 days | salpingoplasty | * | mediocre |
| 7 | 33 | 10 days | salpingoplasty | * | mediocre |

*associated therapy for all patients who have undergone operation:
tetracyclines - cephalosporins
wash (placebo)

TABLE 2

Case characteristics: Group b (surgical group treated with ARFEN)

| Case No. | Age (years) | Therapy duration | Type of operation | Associated therapy | Clinical judgement |
|---|---|---|---|---|---|
| 8 | 25 | 10 days | salpingoplasty | * | excellent |
| 9 | 58 | 10 days | colpohysterectomy | * | excellent |
| 10 | 47 | 10 days | vaginal hysterectomy | * | excellent |
| 11 | 32 | 10 days | salpingoplasty | * | excellent |
| 12 | 31 | 10 days | vulvectomy | * | excellent |
| 13 | 24 | 10 days | metroplasty | * | excellent |
| 14 | 19 | 10 days | ovarian cyst removal | * | excellent |

TABLE 2-continued

Case characteristics: Group b (surgical group treated with ARFEN)

| Case No. | Age (years) | Therapy duration | Type of operation | Associated therapy | Clinical judgement |
|---|---|---|---|---|---|
| 15 | 35 | 10 days | salpingoplasty | * | excellent |

*associated therapy for all patients who have undergone operation: tetracyclines - cephalosporins wash (ARFEN)

TABLE 3

Case characteristics: Group c (medical group treated with placebo)

| Case No. | Age (years) | Therapy duration | Type of operation | Associated therapy | Clinical judgement |
|---|---|---|---|---|---|
| 16 | 22 | 10 days | cervico-vaginitis | * | good |
| 17 | 43 | 10 days | aspecific leukorrhea | * | good |
| 18 | 26 | 10 days | vaginitis | * | good |
| 19 | 33 | 10 days | cervico-vaginitis | * | mediocre |
| 20 | 23 | 10 days | cervico-vaginitis | * | good |
| 21 | 28 | 10 days | cervico-vaginitis | * | mediocre |
| 22 | 36 | 10 days | cervico-vaginitis | * | mediocre |
| 23 | 34 | 10 days | cervico-vaginitis | * | mediocre |

*associated therapy for all patients treated with antibiotics and/or antifungins

TABLE 4

Case characteristics: Group d (medical group treated with ARFEN)

| Case No. | Age (years) | Therapy duration | Type of operation | Associated therapy | Clinical judgement |
|---|---|---|---|---|---|
| 24 | 21 | 10 days | cervico-vaginitis | * | excellent |
| 25 | 31 | 10 days | cervico-vaginitis | * | excellent |
| 26 | 24 | 10 days | leukorrhea, cervicitis | * | excellent |
| 27 | 31 | 10 days | leukorrhea, cytolysis | * | excellent |
| 28 | 42 | 10 days | cervico-vaginitis | * | excellent |
| 29 | 28 | 10 days | cervico-vaginitis | * | excellent |
| 30 | 38 | 10 days | cervico-vaginitis | * | excellent |

*associated therapy for all patients treated with antibiotics and/or antifungins With regard specifically to the antiphlogistic effectiveness of the preparation the result is positive, a clear improvement in all the analysed symptoms having been noted after the initial checks. The same patients received a favourable impression of the pharmacological effect, this being apparent even on the third day following commencement of the applications (first check after basal).

The final clinical judgement was excellent for all patients of groups (b) and (d) treated with ARFEN, whereas it was good, mediocre or insufficient for patients of groups (a) and (c) treated with placebo.

The biometric evaluation of the individual data is analysed hereinafter.

The results are given in Tables 5 and 6 for the medical groups (c) and (d) and for the surgical groups (a) and (b) respectively. The pattern of the various symptomatologic parameters studied, namely irritation, smarting, pain and leukorrhea, was in all cases compared in the two groups, ie the group treated with ARFEN and the group treated with placebo respectively, in order to note the differences.

Comparison at basal time demonstrated the perfect homogeneity of the two groups, as was in fact predictable seeing that assigning of the individual treatments was made with full respect for random distribution.

TABLE 5

Statistical results of symptomatologic parameters (M ± s.d.): Group d (medical group treated with ARFEN) Group c (medical group treated with placebo)

| Days | 0 | | 3 | | 5 | | 7 | | 10 | |
|---|---|---|---|---|---|---|---|---|---|---|
| Group | (d) | (c) | (d) | (c) | (d) | (c) | (d) | (c) | (d) | (c) |
| Irritation | 1.14 ± 0.98 | 1.25 ± 0.96 | 0.85 ± 0.49 | 0.88 ± 0.78 | 0.14 ± 0.35 | 0.50 ± 0.50 | 0.00 | 0.00 | 0.00 | 0.00 |
| Smarting | 1.85 ± 1.24 | 1.50 ± 1.00 | 0.57 ± 0.49 | 1.25 ± 0.96 | 0.28 ± 0.45 | 0.87 ± 0.95 | 0.14 ± 0.35 | 0.25 ± 0.43 | 0.28 ± 0.45 | 0.12 ± 0.33 |
| Pain | 0.71 ± 0.69 | 1.00 ± 1.11 | 0.42 ± 0.49 | 1.00 ± 1.11 | 0.42 ± 0.49 | 0.87 ± 0.78 | 0.00 | 0.12 ± 0.33 | 0.00 | 0.00 |
| Leukorrhea | 2.42 ± 0.49 | 2.37 ± 0.69 | 1.85 ± 0.63 | 2.00 ± 0.70 | 1.23 ± 0.70 | 1.75 ± 0.66 | 0.70 ± 0.70 | 0.87 ± 0.78 | 0.42 ± 0.72 | 0.50 ± 0.70 |

TABLE 6

Vaginitis: statistical results of symptomatologic parameters (M ± s.d.): Group b (surgical group treated with ARFEN) Group a (surgical group treated with placebo)

| Days | 0 | | 1 | | 3 | | 5 | | 7 | | 10 | |
|---|---|---|---|---|---|---|---|---|---|---|---|---|
| Group | (b) | (a) | (b) | (a) | (b) | (a) | (b) | (a) | (b) | (a) | (b) | (a) |
| Irritation | 0.00 | 0.28 ± 0.45 * | 0.00 | 0.57 ± 0.90 * | 0.00 | 0.57 ± 0.90 * | 0.12 ± 0.33 | 0.42 ± 0.72 | 0.00 | 0.42 ± 0.72 | 0.00 | 0.14 ± 0.35 |
| Smarting | 0.00 | 0.85 ± 0.98 * | 2.87 ± 0.33 | 2.57 ± 0.49 * | 1.13 ± 0.78 | 2.00 ± 0.00 ** | 0.25 ± 0.43 | 1.71 ± 0.45 ** | 0.13 ± 0.33 | 0.85 ± 0.34 ** | 0.00 | ± 0.49 ** |
| Pain | 0.00 | 0.57 ± 1.04 | 2.75 ± 0.43 | 2.85 ± 0.35 | 0.87 ± 0.60 | 2.57 ± 0.72 | 0.25 ± 0.43 | 1.71 ± 0.45 | 0.12 ± 0.33 | 1.14 ± 0.63 | 0.00 | 0.85 ± 0.63 |

TABLE 6-continued

| | Vaginitis: statistical results of symptomatologic parameters (M ± s.d.): Group b (surgical group treated with ARFEN) Group a (surgical group treated with placebo) | | | | | | | | | | |
|---|---|---|---|---|---|---|---|---|---|---|---|
| Days | 0 | | 1 | | 3 | | 5 | | 7 | | 10 | |
| Group | (b) | (a) | (b) | (a) | (b) | (a) | (b) | (a) | (b) | (a) | (b) | (a) |
| | * | | | | ** | | ** | | ** | | ** | |
| Leukorrhea | 1.75 ± 0.83 | 2.00 ± 1.07 | 1.50 ± 0.70 | 2.57 ± 0.49 | 0.62 ± 0.48 | 1.85 ± 0.35 | 0.25 ± 0.43 | 1.14 ± 0.63 | 0.12 ± 0.33 | 0.85 ± 0.63 | 0.00 | 0.42 ± 0.49 |
| | | | | ** | | ** | | ** | | | | |

*$p < 0.05$
**$p < 0.001$

Table 5 shows the results of the statistical analysis applied to each of the times considered. It can be observed that for each parameter, group (d) treated with ARFEN showed an intensity which gradually diminished with a consequent continuous reduction in mean numerical values, such that by the 2nd check (5th day) the intensity had fallen practically to zero, making any evaluation for subsequent times impossible. The 5th day could therefore be reliably considered as the last evaluation of each parameter. In group (c), treated with placebo, complete remission of symptomatology was observed only on the 7th-10th day.

Table 6 also shows more rapid and intense action in the treatment of group (b), treated with ARFEN, compared with group (a) treated with placebo.

These results are surprising and confirm the advisability of always effecting pre-post operative prophylaxis aimed at reducing phlogistic-reactive phenomena which are so widespread in gynelogical surgery.

The systemic tolerance towards treatment with ARFEN proved excellent, and Table 7 shows the mean values before and after therapy and the relative comparisons (Student "t").

In these patients, it was also noted that the course of the cicatrization phase was decidedly more imposing in the group treated with ARFEN.

The favourable evolution of the clinical symptoms, the more rapid cicatrization phase and the good local and systemic tolerance point to the conclusion that the wash containing ARFEN is particularly suitable for antiphlogistic treatment in topical gynelogical therapy, both in pathologies of medical pertinence and in pathologies of surgical pertinence. To these situations must obviously be added childbirth, for which the wash allows the anatomical structures concerned not only to be cleaned but in particular to be disinflamed. Finally, ARFEN is active both in aspecific inflammatory forms of functional organic etiology, and in specific inflammatory forms of infective etiology, and can therefore be used as a first-instance medicament while awaiting knowledge of the exact etiology of the phlogosis.

I claim:

1. A composition for vaginal topical use for the local and targeted anti-inflammatory treatment of pathologies of obstretic and gynecological type, comprising lysine p-isobutylphenylpropionate, characterised in that

| Systemic tolerance: Hematological and hematochemical examination results (M ± s.d.) | | | | |
|---|---|---|---|---|
| | Parameters | | | |
| | A1 | | A2 | |
| | Before | After | Before | After |
| Leukocytes | 6.91 ± 1.35 | 9.25 ± 3.18* | 7.4 ± 1.70 | 8.14 ± 2.74 |
| Erythrocytes | 4.42 ± 0.27 | 4.30 ± 0.33 | 4.36 ± 0.37* | 4.16 ± 0.48 |
| Hemoglobin | 13.10 ± 0.75 | 12.92 ± 0.79 | 13.05 ± 0.60 | 12.34 ± 1.23* |
| Hematocrit | 33.56 ± 2.57 | 37.20 ± 2.33 | 36.82 ± 3.10 | 34.26 ± 3.89** |
| Platelets | 266.27 ± 54.05 | 269.26 ± 53.62 | 282.00 ± 36.38 | 285.13 ± 30.89 |
| Glycemia | 78.93 ± 9.97 | 83.20 ± 13.38 | 80.53 ± 13.11 | 79.83 ± 13.81 |
| Azotemia | 0.33 ± 0.09 | 0.30 ± 0.17 | 0.29 ± 0.08 | 0.24 ± 0.08* |
| Creatininemia | 0.74 ± 0.09 | 0.77 ± 0.07 | 0.79 ± 0.11 | 0.86 ± 0.14 |
| GOT | 13.73 ± 6.00 | 10.46 ± 3.30 | 10.53 ± 4.84 | 8.78 ± 3.62 |
| GPT | 13.60 ± 8.22 | 8.86 ± 3.75 | 10.26 ± 4.23 | 10.06 ± 3.02 |
| Alkaline phosphatase | 62.33 ± 9.89 | 65.60 ± 7.62 | 69.93 ± 14.26 | 66.60 ± 21.76 |
| Vricemia | 2.79 ± 0.36 | 2.82 ± 0.28 | 2.76 ± 0.42 | 2.82 ± 0.36 |

*$p < 0.05$
**$p < 0.01$

Table 7 shows some statistically significant differences, which are however of difficult interpretation as the laboratory data were always within normal limits. In addition, certain variations could be closely related to the same pathology such as leukocytis, which is certainly consequent on the surgical operation. We can cite for example azotemia, hematocrit and hemoglobin in the group treated with placebo, for which, although a statistically significant difference is found, the values fall within the norm.

From the local aspect, in no case were undesirable manifestations found which could lead one to suppose poor product manageability.

A consideration which emerged particularly for the group of patients subjected to surgical operation was the favourable effect of slight analgesia.

the lysine p-isobutylphenylpropionate is formulated in aqueous solution with the following substances and relative proportions:
lysine p-isobutylphenylpropionate: 0.5-2.0 g
trimethylcetylammonium p-toluenesulphonate: 0.005-0.02 g
red rose perfume: 0.05-0.2 ml
distilled water: to make up to 100.0 ml.

2. A composition for vaginal topical use for the local and targeted anti-inflammatory treatment of pathologies of obstetric and gynecological type, comprising lysine p-isobutylphenylpropionate, characterised in that the lysine p-isobutylphenylpropionate is formulated in a pharmaceutical form for vaginal use selected from the group consisting of globules and suppositories.

* * * * *